(12) United States Patent
De Voss

(10) Patent No.: US 6,467,484 B1
(45) Date of Patent: Oct. 22, 2002

(54) DEVICE FOR PREVENTING STERTOROUS BREATHING OR SNORING AND FOR PREVENTING ABRASION OF THE TEETH DURING SLEEP

(76) Inventor: Torsten De Voss, Engkaer 22, Hvidovre DK-2650 (DK)

( * ) Notice: Subject to any disclaimer, the term of this patent is extended or adjusted under 35 U.S.C. 154(b) by 0 days.

(21) Appl. No.: 08/849,286

(22) PCT Filed: Oct. 19, 1995

(86) PCT No.: PCT/DK95/00420

§ 371 (c)(1), (2), (4) Date: Jun. 26, 1998

(87) PCT Pub. No.: WO96/16618

PCT Pub. Date: Jun. 6, 1996

(30) Foreign Application Priority Data

| Dec. 1, 1994 | (DK) | 1371194 |
| Mar. 23, 1995 | (DK) | 0300195 |
| Jun. 26, 1995 | (DK) | 9500242 U |

(51) Int. Cl.⁷ ................................................. A61F 5/56
(52) U.S. Cl. ..................... 128/848; 128/860; 602/902
(58) Field of Search ............................... 128/846, 848, 128/859–862; 602/902

(56) References Cited

U.S. PATENT DOCUMENTS

| 2,966,908 A | 1/1961 | Catheart |
| 3,096,761 A | 7/1963 | Moffett |
| 3,132,647 A | 5/1964 | Corniello |
| 3,314,423 A | 4/1967 | Boatwright |
| 3,871,370 A | * 3/1975 | McDonald ................... 128/860 |
| 4,718,662 A | * 1/1988 | North ........................... 128/860 |
| 4,901,737 A | 2/1990 | Toone |
| 5,666,973 A | * 9/1997 | Walter ......................... 128/860 |

FOREIGN PATENT DOCUMENTS

| DE | 407949 | 1/1925 |
| DE | 0182387 | * 11/1985 |
| DE | 3816769 A1 | 8/1989 |
| DE | 3816769 | 8/1989 |
| EP | 0 182 387 | 5/1986 |
| EP | 0 337 201 | 10/1989 |
| GB | 2 264 868 | 9/1993 |
| WO | 9013276 | 11/1990 |

* cited by examiner

Primary Examiner—Michael A. Brown
Assistant Examiner—Sharon N. Thornton

(57) ABSTRACT

Device for prevention of sterotorous breathing or snoring and adapted to be fixed in a person's upper part of the mouth and being characterized in comprising a non-rigid and flexible transverse girder for fixation in the upper part of a person's mouth, preferably at the back of the upper part of the mouth, and a tongue catching member extending downwardly from the non-rigid and flexible transverse girder and produced from an elastic material and which is adapted to fixate the tongue in a forward position so that it does not block the respiratory passages.

20 Claims, 7 Drawing Sheets

Figure 1:
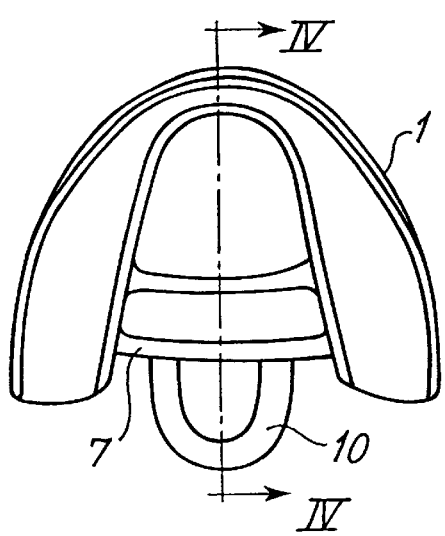

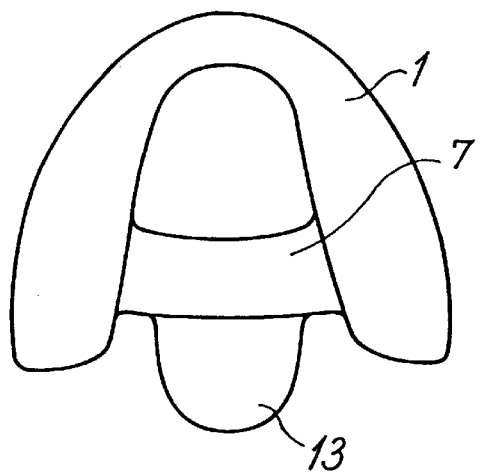
Fig. 9
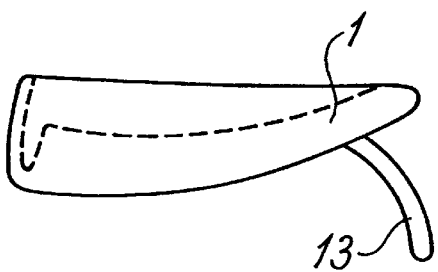
Fig. 10
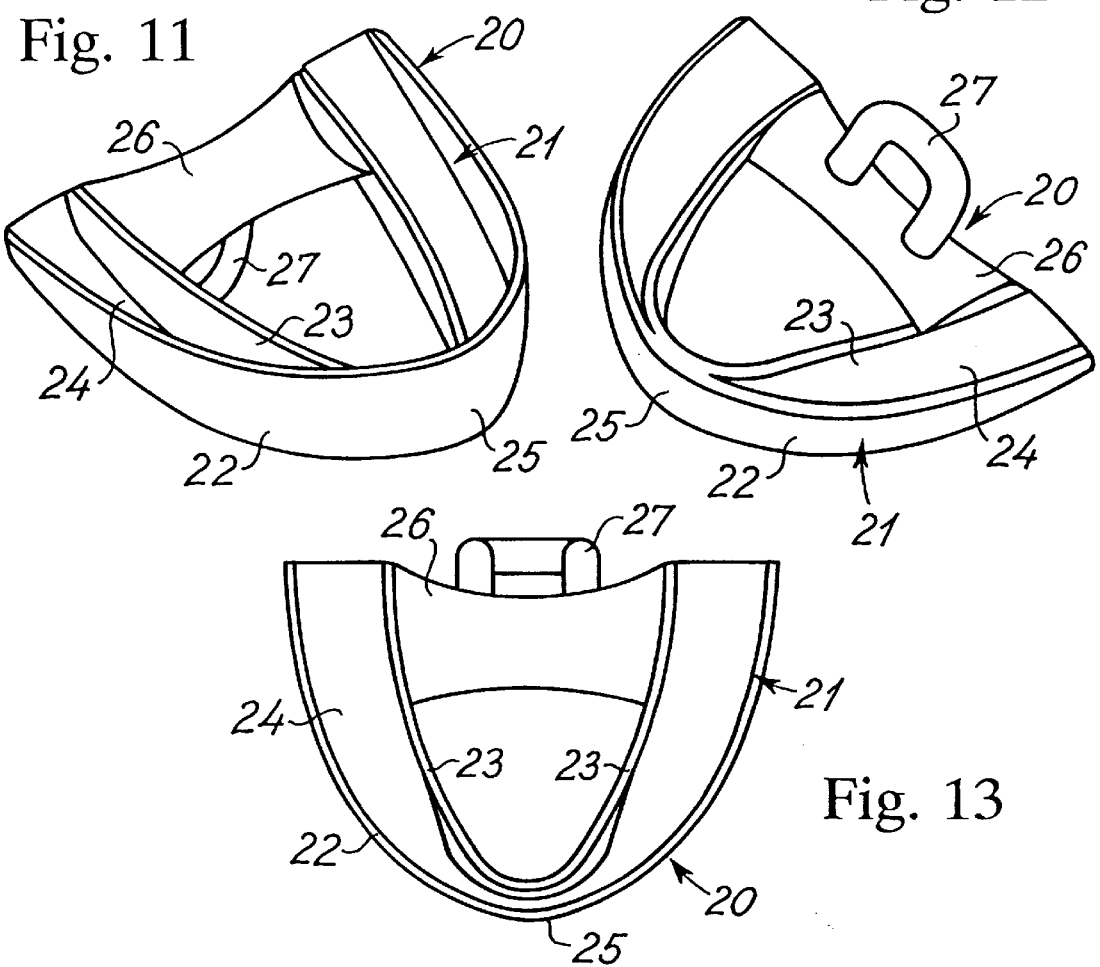
Fig. 11
Fig. 12
Fig. 13

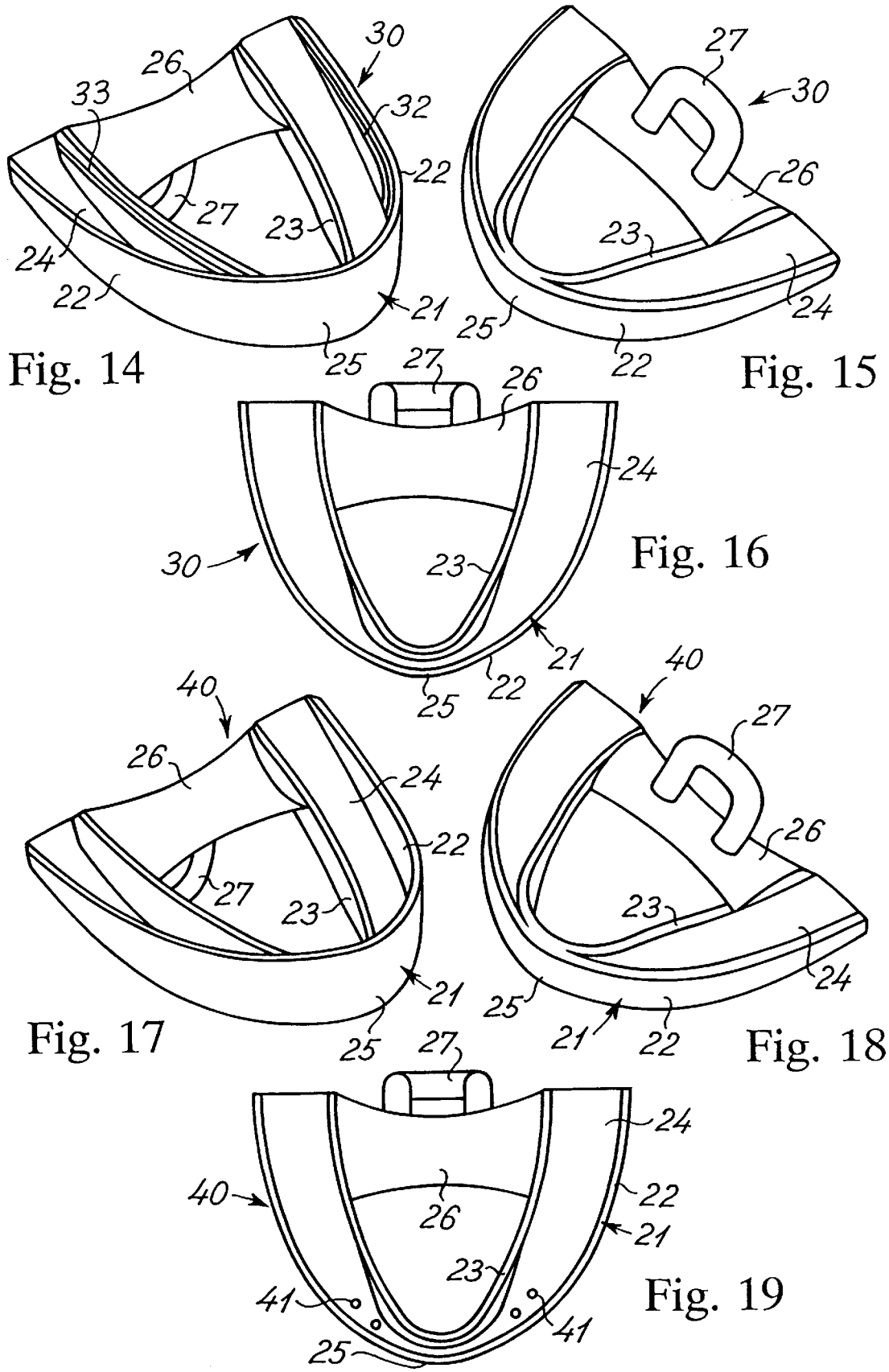

DEVICE FOR PREVENTING STERTOROUS BREATHING OR SNORING AND FOR PREVENTING ABRASION OF THE TEETH DURING SLEEP

The present invention relates to a device for preventing stertorous breathing or snoring and adapted to be fixated to a person's upper row of teeth and having a retaining means for fixating the tongue in a forward position in order to prevent the tongue from blocking the respiratory passages.

The present invention furthermore relates to a device for preventing abrasion of the teeth in the upper and lower parts of the mouth as a result of a person's grinding his or her teeth during sleep.

Numerous devices of this kind are already known, however they all suffer from the disadvantage that they have to be manufactured especially for the individual user or at least have to be adjusted to the user by people skilled in the art.

Furthermore, the known devices for prevention of stertorous breathing or snoring often suffer from the disadvantage or drawback that the device is not comfortable to wear and in some instances prevent the user from sleeping.

Known devices and known techniques of preventing stertorous breathing or snoring are described in DE 407.449, U.S. Pat. No. 3,132,647, DE 3816769 and DE 4026402 and devices for preventing abrasion of the teeth during sleep are known from and described in U.S. Pat. Nos. 2,966,908, 3,096,761 and 3,314,423 to which patent applications and patents reference is made and which US-patents are hereby further incorporated in the present specification by reference.

An object of the invention is to provide a device of the above mentioned kind which device can be used without professional assistance, which is not inconvenient to wear and which does not damage the soft or hard tissue of the oral cavity.

The above objects together with numerous other objects, advantages and features which will be evident from the below detailed description of presently preferred embodiments of the device according to the present invention are obtained by a device according to a first aspect of the present invention for preventing stertorous breathing and snoring comprising a non-rigid and flexible transverse girder for fixation in the upper part of a person's mouth, preferably at the back of the upper part of the mouth, and a tongue catching member extending downwardly from the non-rigid and flexible transverse girder the tongue catching member being produced from an elastic material and being adapted to fixate the tongue in a forward position in order to prevent the tongue from blocking the respiratory passages.

Due to the elasticity of the tongue catching member, the device according to the present invention may be used by a variety of individuals without the necessity of having the device adjusted individually to the intentional user. Furthermore, the elasticity of the tongue catching means allows the user to swallow while the device according to the present invention is positioned in its intentional position in the upper part of the person's or user's mouth without causing any substantial uncomfort to the user or person wearing or using the device.

It is further contemplated that the device according to the present invention provides a safety or security advantage as the tongue catching member of the device according to the present invention may prevent the tongue from falling backwards and block the respiratory passages when the user yawns during sleep.

The device according to the present invention may be produced from any appropriate natural or synthetic material or materials, such as synthetic or natural rubber, e.g. medical rubber, or plastics materials, such as polyvinyl plastics material including vinyl acetate ethylene polymeric material as e.g. polyethylene vinyl acetate or a polyefine such as polyethylene or polypropylene. Due to the elasticity and flexibility of the material, the soft and hard tissue of the oral cavity is not damaged by the device according to the present invention. It is especially preferred that the polymeric material is a thermo plastic polymeric material. The ability of the device according to the present invention to adapt to the specific set of teeth or gums of the intentional user or person wearing the device according to the present invention may be further improved by utilizing a polymeric material which softens at a temperature of between 40 and 80° C. and preferably between 50 and 70° C., and plastically adjust to the teeth or gums of the user in question. Examples of polymeric materials of this type are materials produced and marketed by the company Bayer Dental™ under the trademarks MEMOSIL® C. D. and PROVIL® P. soft. The above polymeric materials or similar polymeric materials may further be used in combination with a precast device including a recess or a groove for receiving the softenable polymeric material. The device according to the present invention is preferably produced by casting e.g. by diecasting as the device in its entirety is preferably integrally cast from an elastic material, e.g. natural or synthetic rubber or one of the above mentioned plastics materials or a combination thereof. By means of devices provided in the die a marking indicating the time of production may be obtained.

According to the present invention, the non-rigid and flexible transverse girder may be fixated in the upper part of a person's mouth by means of a fixation member adapted to cooperate with the teeth or the gums in the upper part of the user's mouth. According to one embodiment of the device according to the invention, the non-rigid and flexible transverse girder and the downwardly protruding tongue catching member may be produced from the same non-rigid and flexible material. Moreover, the fixation member may be adapted to engage with the teeth and/or the gums in the upper part of a user's mouth for fixation of the embodiment in the upper part of the user's mouth, and it may be produced from an elastic material for adjustment to the row of teeth and the gums in the upper part of the user's mouth.

According to a presently preferred embodiment of the device according to the invention, the fixation member may be U-shaped and constitute a groove for engaging with the user's teeth or gums and optionally for receiving the above mentioned softenable polymeric material. The groove may be perforated or provided with slots for fixation in relation to the users teeth and/or gums. It is i.a. the object of the perforation to ensure a suitable air inlet to the gums, while it is the aim of the slots to ensure that the positioning of the device is established through snap fitting.

In one embodiment, the transverse girder may be more rigid than the U-shaped groove, and it may be of a rigidity so as to ensure that the two legs of the groove are substantially kept at the same lavel during use of the device. Thus, the U-shaped groove is prevented from twisting during use whereby the risk that the device unintendedly loses its engagement with the upper row of teeth is to a substantial extent eliminated. The lower surface of the transverse girder may be rounded off in order for the tongue to rest comfortably between the transverse girder and the front teeth when being pressed forwardly by the retaining member.

The tongue catching member may be of any appropriate shape which is not inconvenient for the user, i.g. be of the shape of a plate with rounded edges. It is especially preferred that the tongue catching member is produced as a substantially U-shaped brace.

In profile, the tongue catching member may be of any appropriate shape causing the tongue to be pressed forwardly during use of the device, i.e. arc-shaped having its cavity downwards.

Furthermore, the tongue catching member according to the present invention may extend crosswise backwardly and downwards.

Still further, according to the presently preferred embodiment of the device according to the present invention, the exterior wall of the U-shaped member, at least where it is adjusted to engange with the front teeth, may extend upwardly and inwardly in relation to its bottom wall in such a manner that it is pressed outwardly during positioning of the device and also after positioning of the device puts a pressure to the front teeth for fixation of the device.

Furthermore, according to the presently preferred embodiment of the device according to the present invention, the interior side wall of the U-shaped part may be lower than the exterior side wall at least in the area which is adapted to engage with the front teeth.

The tongue catching member is preferably adapted to engage with the upper surface of the tongue at a distance from the root of the tongue and preferably in the area between the premolar and a distance behind the molar.

Preferably, the U-shaped groove may be provided so as to engage with or cover all the teeth of an average user. However, it should preferably not cover the entire molar. Thus, it is noted that when producing the device it is an advantage that children's and grown-up's sets of teeth are substantially of the same size and thus the device may be produced in only few standard sizes.

Furthermore, the device according to the invention may comprise a catching member extending outwardly from the front wall of the U-shaped groove in the area of the U-shaped wall which is adapted to engage with the front teeth. This embodiment of the present invention is especially intended to be used in recovery wards as in this event the device may be removed from a patient's mouth by grasping the catching member.

According to a further embodiment of the device according to the present invention, the device further comprises an additional fixation member adapted to cooperate with the teeth or the gums in the lower part of the user's mouth, the additional fixation member being connected to the fixation member through a hinge and serving the purpose of fixating the lower part of the user's mouth in relation to the upper part of the user's mouth, preferably in a relaxed position. The provision of the additional fixation member provides a device allowing the lower part of the users mouth to be fixated in relation to the upper part of the user's mouth when the device is positioned in its intentional position in the mouth of the user or person using the device. The additional fixation member may be utilized for fixating the lower part of the user's mouth in any specific position e.g. a forward or rearward position dependent on the geometrical shape and configuration of the additional fixation member relative to the fixation member adapted to cooperate with the teeth and/or the gums in the upper part of the user's mouth. The provision of the additional fixation member, thus, renders it possible to fulfill certain clinical objects, however the additional fixation member preferably allows the user to freely open or close his or her mouth during the sleep, e.g; for allowing the user to swallow and/or yawn. Therefore the additional fixation member mainly constitutes a means for preventing the lower part of the user's mouth to be positioned in an extreme position such as an extreme rearward or forward position which might cause harm or injuries or simple discomfort to the user.

The above objects together with numerous other objects, advantages and features which would be evident from the below detailed description of presently preferred embodiments of the device according to the present invention are obatined by a device according to a second aspect of the present invention for preventing abrasion of the teeth in the upper and the lower part of the mouth as a result of a person grinding his teenth during sleep, comprising a U-shaped fixation part constituting a groove for catching the user's teeth and gums in the upper part of the user's mouth and being produced from a elastic material for adjustment in relation to the row of teeth and the gums in the upper part of the user's mouth, and further comprising a non-rigid and flexible transverse girder connecting the back ends of the U-shaped fixation part in the back of the upper part of the user's mouth.

According to a preferred embodiment of the device according to the present invention, the groove may be perforated or provided with slots for fixation in relation to the teeth and/or the gums of the user. The perforations may i.a. ensure a suitable air input to the gums while the slots ensure the positioning of the device to be established to take place through snap fitting. Furthermore, the fixation member may comprise a tongue catching member extending downwardly from the non-rigid and flexible transverse girder which tongue catching member is produced from an elastic material and is adapted to keep the tongue in a forward position in order to prevent the tongue from blocking the respiratory passages.

Figure 2:
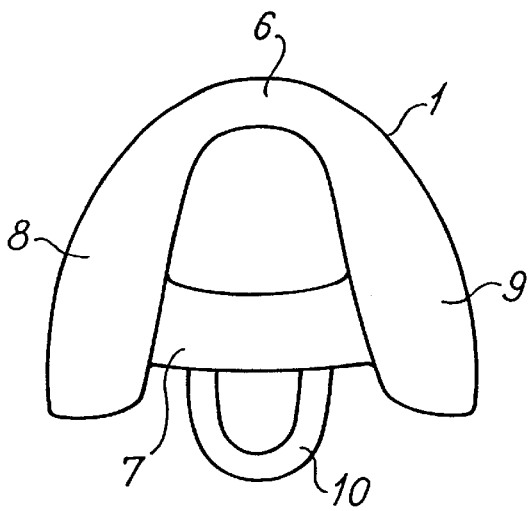
Figure 3:
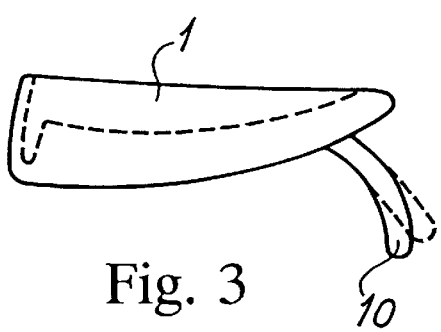
Figure 4:
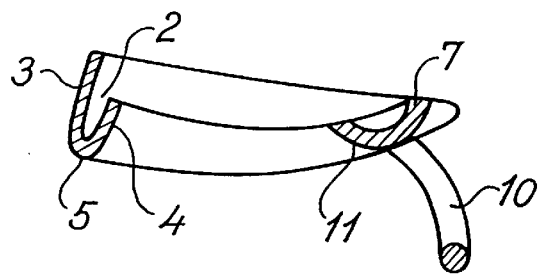
Figure 7:
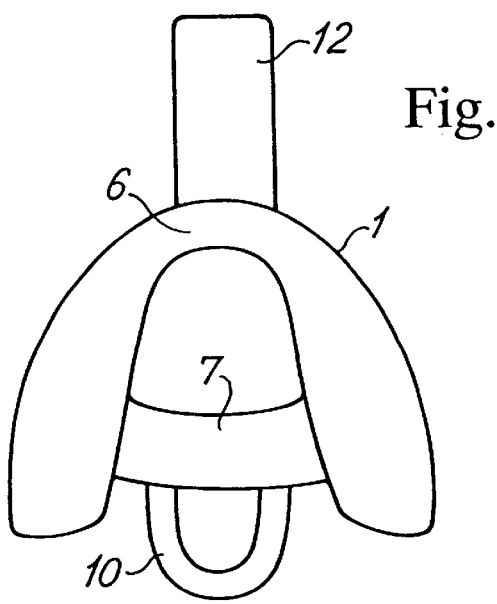
Figure 8:
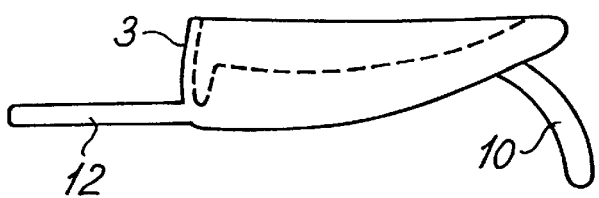
Figure 5:
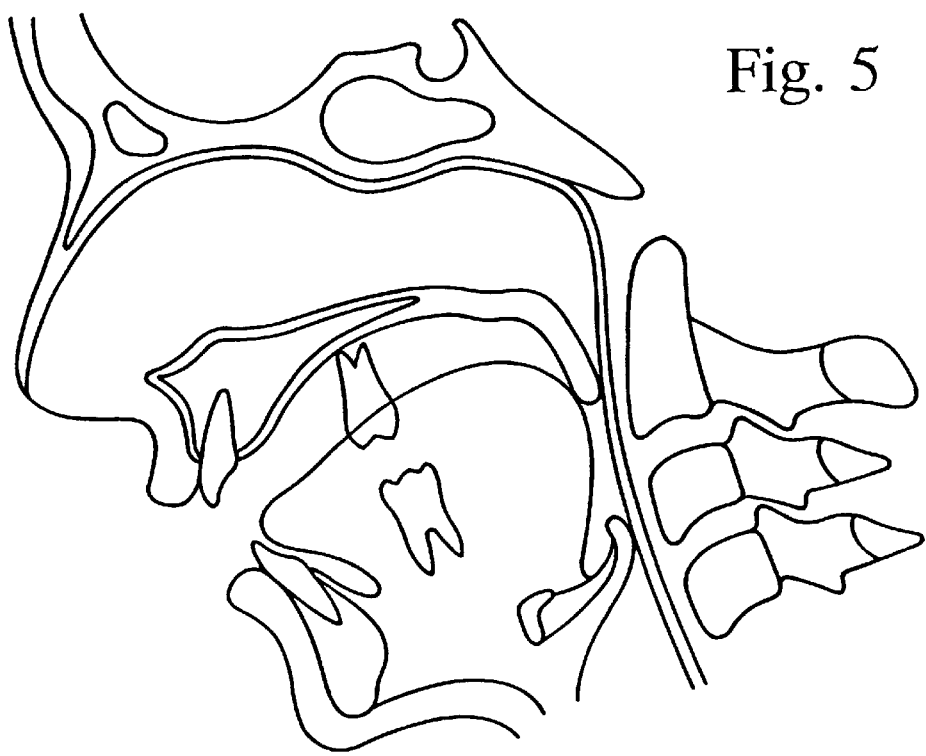
Figure 6:
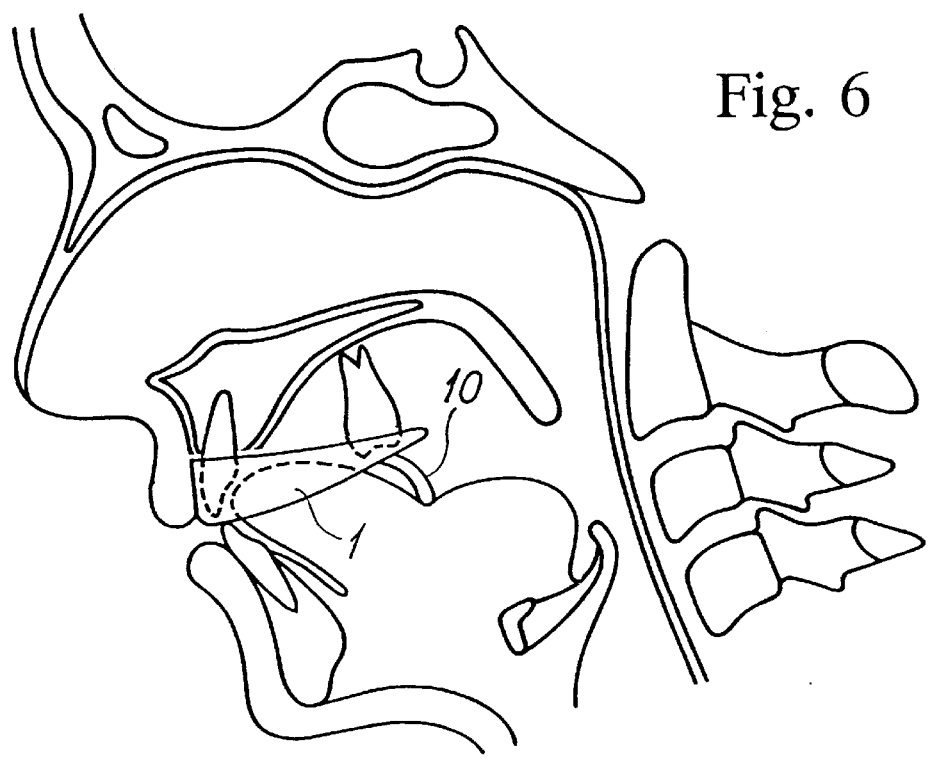

The present invention will be described in further details below with reference to the drawings in which FIG. 1 is a top view of a first embodiment of the device according to the present invention for preventing stertorous breathing or snoring and also for preventing abrasion of the teeth in the user's mouth, FIG. 2 is a bottom view of the first embodiment of the device illustrated in FIG. 1, FIG. 3 is a side or elevational view of the first embodiment of the device seen from the right side in FIG. 1, FIG. 4 is a sectional view of the first embodiment of the device along the line IV—IV in FIG. 1, FIG. 5 is a schematical and sectional view of the cranium of a person illustrating the tongue falling back and blocking the respiratory passages when the person is lying on his back with his or her mouth open, FIG. 6 is a schematic and sectional view similar to the view of FIG. 5, illustrating the function of the first embodiment of the device according to the present invention of keeping the person's tongue in a forward position and ensuring an open respiratory passage, FIG. 7 is a bottom view similar to the view of FIG. 2 of a second embodiment for the device according to the present invention, FIG. 8 is a side and elevational view similar to the view of FIG. 3 of the second embodiment of the device FIG. 9 is a bottom view similar to the views of FIGS. 2 and 7 of a third embodiment of the device according to the present invention, FIG. 10 is a side or elevational view similar to the views of FIGS. 3 and 8 of the third embodiment according to the present invention, FIGS. 11, 12 and 13 are perspective views of a fourth embodiment of the device according to the present invention having a substantially plane transverse girder, FIGS. 14, 15 and 16 are perspective views of a fifth embodiment of the device according to the present invention having elongated slots and grooves on the inner surfaces of the side walls of the U-shaped groove.

Figure 20:
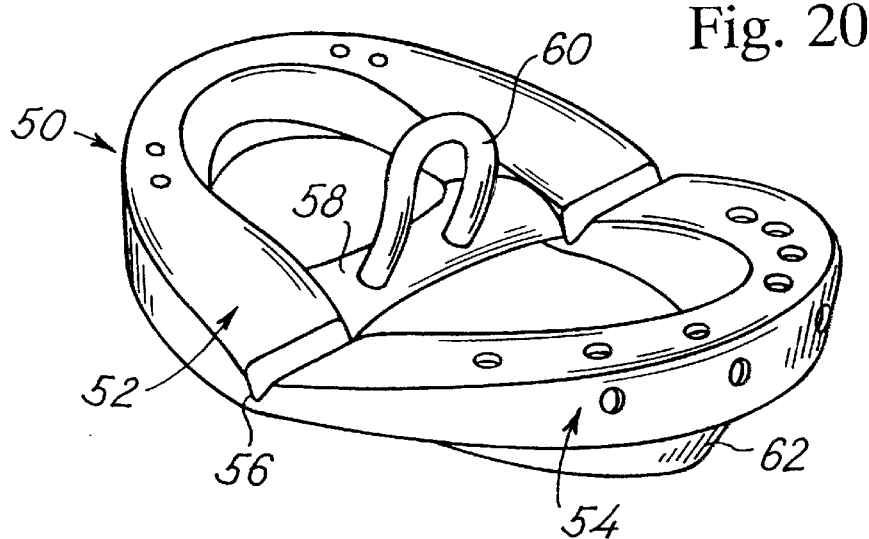
Figure 21:
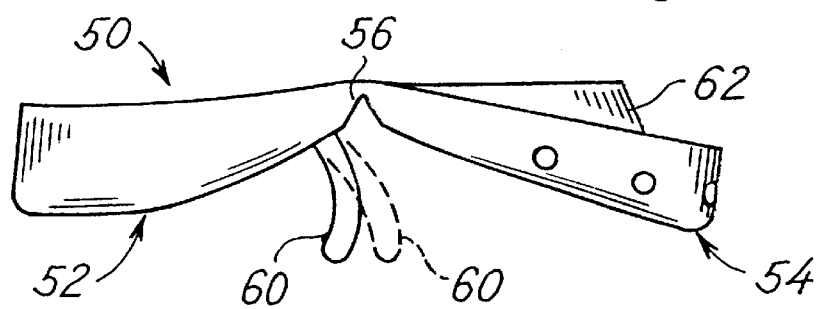
Figure 22:
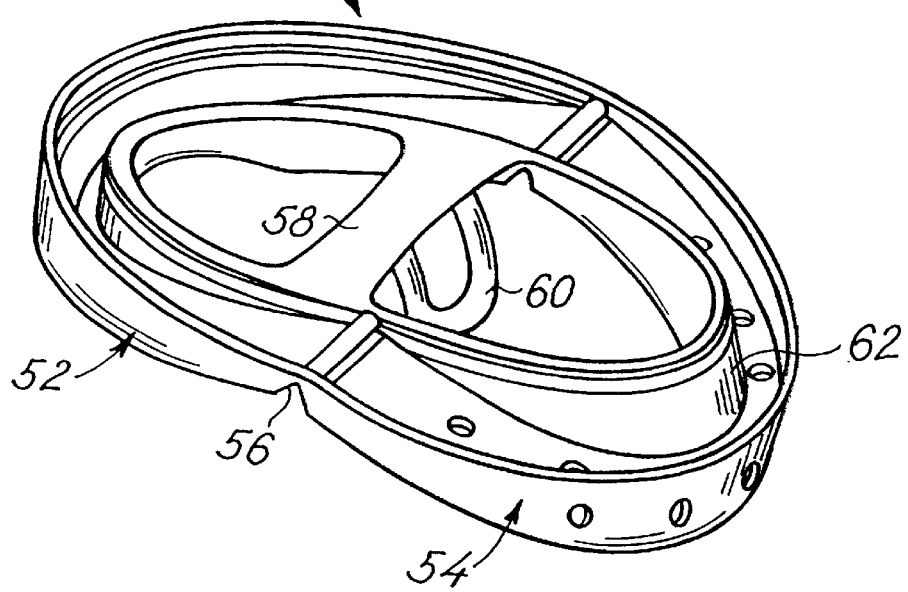
Figure 23:
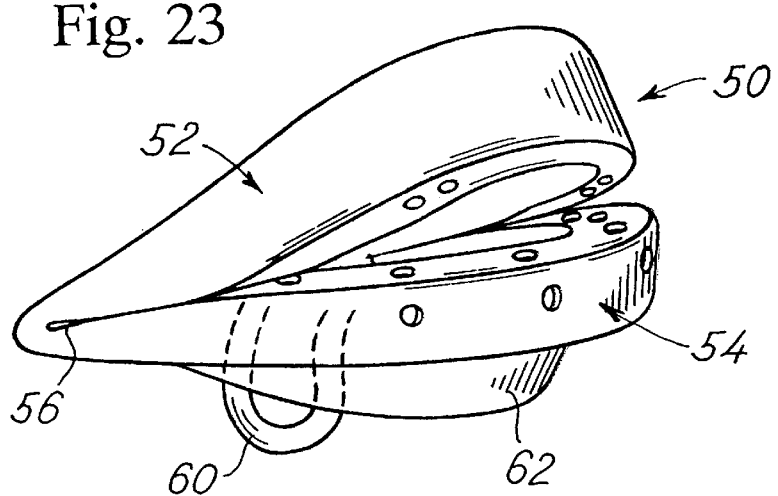
Figure 24:
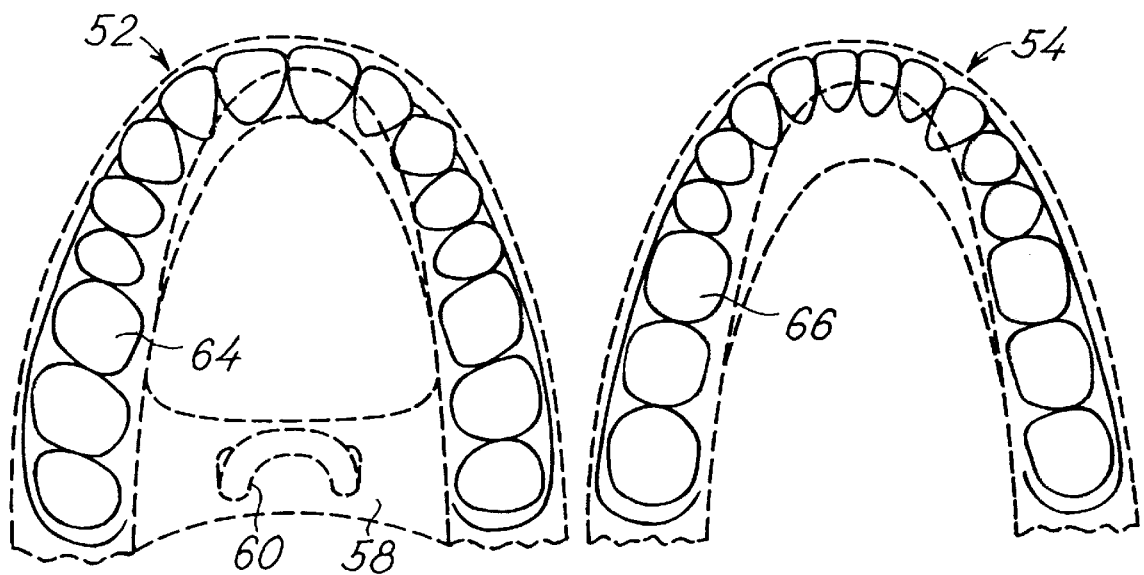
Figure 25:
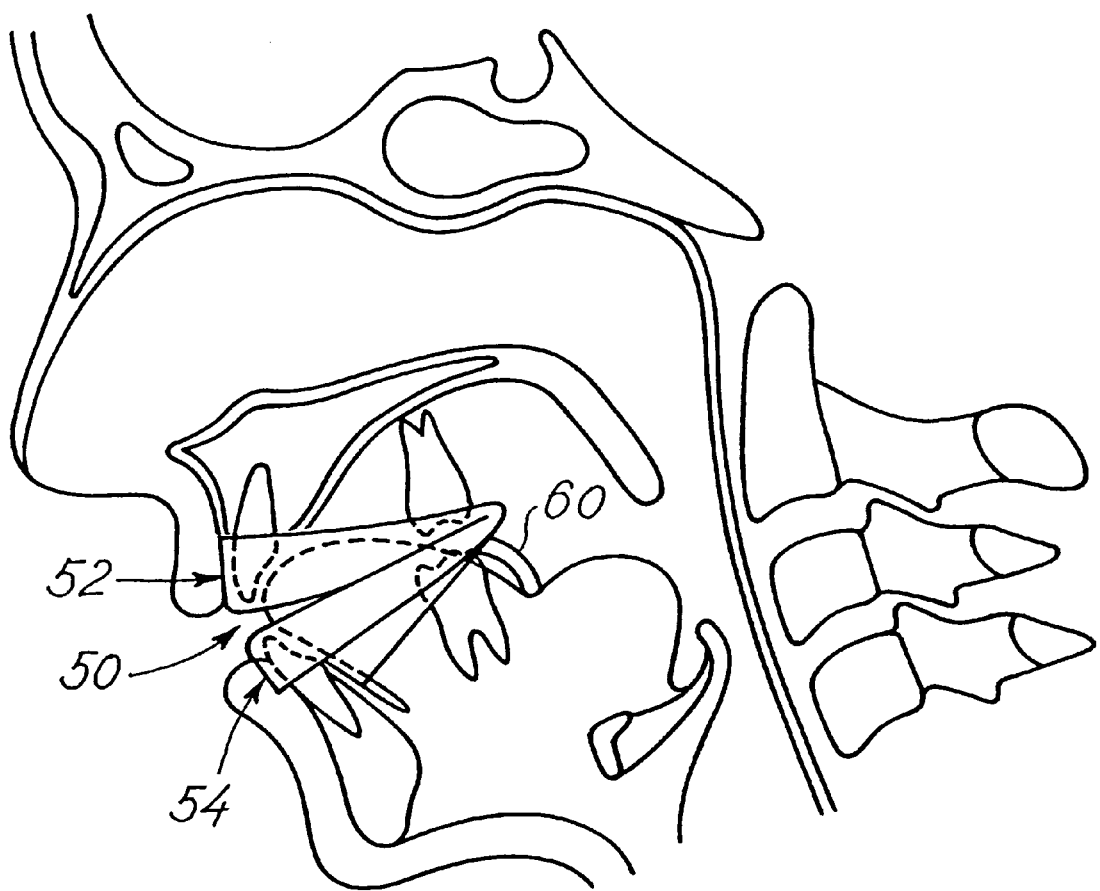

FIGS. 17, 18 and 19 are perspective view of a sixth embodiment of the device according to the present invention having perforations in the front of the bottom wall of the U-shaped groove, FIG. 20 is a schematic and perspective view of a seventh embodiment of the device according to the present invention comprising a top and bottom part for fixating the device relative to the top and bottom part, respectively, of the user's mouth illustrated in an open or relaxed state illustrating a first side of the device, FIG. 21 is a side or elevational view similar to the views of FIGS. 3, 8 and 10 of the seventh embodiment of the device according to the present invention, also illustrating the elastic property of a tongue catching member of the embodiment, FIG. 22 is a perspective and schematic view similar to the view of FIG. 20 illustrating a second side of the device, FIG. 23 is a perspective, schematic and partly sectional view of the seventh embodiment of the device according to the present invention illustrating the device in a closed and unrelaxed state, FIG. 24 is a schematic view illustrating the positioning of the upper and lower parts, respectively, of the seventh embodiment of the device according to the present invention relative to the teeth and/or the gums of the user's mouth, and FIG. 25 is a schematic and sectional view of the cranium of a person similar to the views of FIGS. 5 and 6 illustrating the function of the seventh embodiment of the device according to the present invention.

In FIGS. 1–4, a first embodiment of the device according tot he present invention is shown, comprising a U-shaped fixation member 1 intended to be fixated to a person's upper row of teeth. The U-shaped member 1 substantially has a shape corresponding to the upper row of teeth and is provided with a groove 2 similarly having the shape substantially corresponding to the course of the upper row of teeth. The groove 2 is defined by an exterior side wall 3, an interior side wall 4 and a bottom wall 5. The exterior side wall 3 is relatively thin and flexible and extends upwardly and inwardly from the bottom wall 5 in a foremost arch-shaped area 6 of the U-shaped fixation member 1 in such a manner that when being positioned on the upper row of teeth the device will be pressed outwardly and after the device has been positioned it puts a pressure on the teeth for fixation of the device in relation to the upper row of teeth of the user's mouth.

The interior side wall 4 is substantially shorter than the exterior side wall in order to facilitate the positioning of the device on the upper row of teeth. The lower bottom wall 5 is thicker than the exterior side wall 3.

The U-shaped fixation member 1 defines legs 8, 9 between which a transverse girder 7 extends at the rearmost end of the U-shaped fixation member 1, i.e. opposite to the foremost arch-shaped area 6. The transverse girder 7 is substantially U-shaped and its wall thickness is larger than that of the exterior side wall providing a more stiff or less elastic or flexible structure as compared to the walls 34 of the U-shaped fixation member 4. Thus, the girder 7 provides a certain rigidness or stability so that the U-shaped fixation member is prevented from being deformed when in use. The girder 7 especially ensures that the legs 8, 9 of the U-shaped groove do not twist in relation to one another when in use.

From a lower surface 11 of the girder 7, a U-shaped brace or a tongue catching member 10 extends downwardly and rearwardly serving the purpose of keeping the tongue in a forward position when the device is positioned on a user's upper row of teeth. The U-shaped brace or tongue catching member 10 is of a circular cross-section and seen from the one side it defines an arch having its cavity facing forwards. The U-shaped brace or tongue catching member 10 is of such a flexibility that it bends slightly backwards when being in engagement with the object (illustrated in FIG. 3 by means of dotted lines) and presses the front part of the tongue forward between the transverse girder and the front teeth in such a manner that it will rest in a comfortable way due to the arch-shaped lower surface 11 of the transverse girder 7.

FIG. 5 is a schematic and vertical section view of the cranium of a human being illustrating the upper and lower parts of the mouth of the human being and clearly illustrating the origin of steterous breathing or snoring as the lower part of the mouth falls down and rearwardly and the tongue also slips rearwardly providing a blocking of the respiratory passages of the person when the person is lying on his back with his or her mouth open. FIG. 6 cleraly illustrates the function of the device according to the present invention as the device is positioned fixated relative to the teeth and/or gums of the upper part of the mouth of the person using the device as the U-shaped fixation member 1 positions the device relative to the teeth of the upper part of the user's mouth and as the U-shaped brace or tongue catching member 10 catches the tongue and keeps the tongue in a forward position preventing the tongue from slipping rearwardly providing the blocking state illustrated in FIG. 5. In FIG. 6, the tonge is illustrated in a position in which a free passage is established behind the tongue the person using the device from stertorous breathing or snoring.

A second embodiment of the device according to the present invention is illustrated in FIGS. 7 and 8 and generally the second embodiment of the device corresponds to the first embodiment shown i FIGS. 1–4. However, it has a plate-shaped catching member 12 extending outwardly from the lower end of the exterior side wall 3 in the arch-shaped area 6 of the U-shaped fixation member 1. The second embodiment of the device according to the present invention is especially adapted to and intended to be used in hospitals as by grasping the catching member 12 it is possible to remove the device from a patient without putting one's fingers into his mouth.

A third embodiment of the device according to the present invention is illustrated in FIGS. 9 and 10 and generally corresponds to the first embodiment shown in FIGS. 1–4. However, the U-shaped brace or tongue catching member 10 is substituted by a flexible plate-shaped part 13 extending diagonally backwards and downwards from the transverse girder. Seen from the one side, the plate-shaped part 13 is curved corresponding to the U-shaped brace or tongue catching member 10 in the first embodiment shown in FIGS. 1–4 and similarly serves the purpose of keeping the tongue in a forward position. In order to obtain the intended flexibility, the plate-shaped part 13 is of a reduced thickness as compared to the U-shaped brace or tongue catching member 10.

In FIGS. 11–13, FIGS. 14–16 and FIGS. 17–19, a fourth, a fifth and a sixth embodiment of the device according to the present invention is shown, respectively, designated the reference numerals 20, 30 and 40, respectively. The fourth embodiment 20, the fifth embodiment 30 and the sixth embodiment 40 are of the same general configuration illustrated in FIGS. 11–13 and serve the same purpose as the above described first, second and third embodiments shown in FIGS. 1–4, 7, 8, and 9, 10, respectively.

The fourth embodiment 20, thus, comprises a U-shaped fixation member 21 defining a U-shaped trough or groove for catching around and fixation the device relative to the teeth of the upper part of the mouth of the user or person. The fixation member 24, thus, include an exterior side wall 22, and interior side wall 23 and a bottom wall 24 bridging or interconnecting the exterior side wall 22 and the interior side wall 23. Between the exterior side wall 22 and the interior side wall 23, the above mentioned groove is defined for receiving the teeth of the upper mouth of the person for fixating the entire device 20 relative to the upper mouth of the person or user. Like the above described first embodiment 1, the U-shaped fixation member 1 defines a foremost arch-shaped area or part 25. At the opposite end of the U-shaped fixation member 21, i.e. the end opposite to the foremost arch-shaped area or part 25, a girder 26 brigdes the U-shaped interior side wall 23. From the plane defined by the bottom wall 24, a U-shaped brace or tongue catching member 27 extends downwardly, i.e. in a direction opposite to the upwardly protruding exterior and interior side walls 22 and 23, respectively.

In FIG. 11, the top side of the fourth embodiment 20 of the device according to the present invention is illustrated which top side is intended to be positioned facing upwardly towards the teeth or gums of the upper part of the mouth of the user or person to use the device 20. In FIG. 12, the opposite side or the lower side of the fourth embodiment 20 is shown illustrating in greater details the flexible U-shaped brace or tongue catching member 27. In FIG. 13, a plane top view of the fourth embodiment 20 illustrates the configuration of the interior side wall 23, which configuration assists the interior and exterior side walls 22 and 23 in fixating the device 20 relative to the teeth of the upper part of the user's mouth. It is to be realized that the exterior side wall 22 defines a height exceeding the height of the interior side wall 23, however, the dimensions and geometrical relations of the components of the fourth embodiment 20 shown in FIGS. 11–13 may be modified or altered for complying with specific requirements dictated by the geometry of the cranium or the teeth and/or gums of the user or person using the device.

In FIGS. 14–16, the fifth embodiment 30 of the device according to the present invention is shown. In FIGS. 14–16, components or elements identical to the components or elements of the fourth embodiment 20 described above with reference to FIGS. 11–13 are designated the same reference numerals. The fifth embodiment 30 differs from the above described fourth embodiment in that the interior and exterior side walls 22 and 23 of the U-shaped fixation member 21 are provided with slots or grooves designated the reference numerals 32 and 33, respectively, serving the purpose of improving the fixation of the U-shaped fixation member 21 relative to the teeth or the gums of the upper part of the user's mouth.

In FIGS. 17–19, the sixth embodiment 40 of the device according to the present invention is shown differing from the above described fourth and fifth embodiments 20 and 30, respectively, in that a plurality of apertures or holes are provided in the bottom wall 24 of the U-shaped fixation member 21 which apertures or holes are illustrated in FIG. 19 and one of which is designated the reference numeral 41. The apertures or holes 41 basically constitute venting apertures or holes serving the purpose of venting any air confined above the bottom wall 24 as the embodiment 40 is fixated relative to the teeth and/or gums of the upper part of the user's mouth. Thus, the provision of the venting apertures or holes 41 like the above described grooves 32 and 33 serve the purpose of improving the fixation of the fifth and sixth, respectively, embodiment of the device according to the present invention relative to the teeth or gums of the upper part of the user's mouth as compared to the above described fourth and presently preferred embodiment 20 described above with reference to FIGS. 11–13.

The above described first, second, third, fourth, fifth and sixth embodiments of the device according to the present invention all exhibit the common feature that the device is fixated to the teeth and/or gums of the upper part of the users mouth, exclusively. In FIGS. 23–25, a seventh embodiment and the utilization and function of the seventh embodiment is illustrated which seventh embodiment differs from the above described embodiments in that the seventh embodiment includes no fixation members constituting an upper and a lower fixation member, respectively, for fixating the device according to the present invention relative to the teeth and/or gums of the upper and lower parts, respectively, of the user's mouth.

The seventh embodiment illustrated in FIGS. 20–25 is designated the reference numeral 50 in its entirety. The embodiment 50 comprises an upper U-shaped fixation member 52 and a lower U-shaped fixation member 54 which are integrally cast and interconnected through an integral hinge 56. The upper and lower U-shaped fixation members 52 and 54 are intended and adapted to fixate the device 50 relative to the teeth and/or gums of the upper and lower parts, respectively, of the user's mouth. Basically, the upper and lower U-shaped fixation members 52 and 54 are of identical configuration and of the configuration of the fourth, fifth and sixth embodiments, 20, 30 and 40, respectivly, described above with reference to FIGS. 11–12, 13, 14–16 and 17–19, respectively. Thus, the upper U-shaped fixation member 52 comprises a girder 58 bridging the inner walls of the U-shaped fixation member 52 similar to the girder 26 described above with reference to FIGS. 11–13. From the girder 58, a U-shaped brace or tongue catching member 60 protrudes upwardly as illustrated in FIG. 20 serving the same purpose as the U-shaped brace or tongue catching member 27 described above with reference to FIGS. 11–13.

Contrary to the upper U-shaped fixation member 52, the lower U-shaped fixation member 54 does not include any girder or U-shaped brace or tongue catching member similar to the girder 58 and the member 60, respectively, as the lower U-shaped fixation member has to allow the tongue to be received within the space defined within the interior side wall of the U-shaped fixation member 54 which interior side wall is illustrated in FIG. 21 and designated the reference numeral 62. In FIG. 22, the opposite side of the seventh embodiment 50 of the device according to the present invention is shown disclosing the grooves defined within the upper and lower U-shaped fixation members 52 and 54.

In FIG. 21, a side or elevational view of the seventh embodiment 50 discloses the above mentioned interior side wall 62 of the lower U-shaped fixation member 54 and also discloses the elastic or flexible property of the U-shaped brace or tongue catching member 60 which is illustrated firstly in a full line position in which the U-shaped brace or tongue catching member 60 is in a relaxed state and a dotted line position in which the brace or tongue catching member 60 is bent rearwardly from the relaxed state similar to the state in which the U-shaped brace or tongue catching member 60 is positioned when the device 50 is positioned in the mouth of the user and the U-shaped brace or tongue catching member 60 catches behind the tongue of the user as illustrated in FIG. 25.

In FIG. 23, the function of the hinge 56 of the seventh embodiment 50 of the device according to the present invention is illustrated as the upper U-shaped fixation member 52 is bent from the position shown in FIG. 20 to a position adjacent to the lower U-shaped fixation member 54 which position corresponds to the position in which the device 50 is kept when the device is mounted within the mouth of the user or person as illustrated in FIG. 25. The seventh embodiment 50 is like the above described sixth embodiment 40 described above with reference to FIGS. 17–19 provided with venting apertures or holes provided in the upper or lower U-shaped fixation members 52 and 54, respectively, serving the same purpose as the venting apertures or holes 41 described above with reference to FIG. 19.

FIG. 24 illustrates the intentional position of the upper and lower U-shaped fixation members 52 and 54, respectively, relative to the teeth of the upper and lower parts, respectively, of the user's mouth. In FIG. 24, the reference numeral 64 designates a tooth of the upper part of the user's mouth which tooth together with the remaining teeth of the upper part of the user's mouth are received within the groove defined within the upper U-shaped fixation member 52 as described above with reference to FIGS. 11–13 and 20–23. Similarly, in FIG. 24, the reference numeral 66 designates a tooth of the lower part of the user's mouth which tooth together with the remaining teeth of the lower part of the user's mouth are received within the groove defined within the lower U-shaped fixation member 54 also as described above with reference to FIGS. 11–13 and 20–23. In FIG. 24, the girder 58 and the U-shaped brace or tongue catching member 60 are also illustrated.

It is to be realized that the exterior side walls of the upper and lower U-shaped fixation members 52 and 54, respectively, similar to the exterior side walls 22 of the fourth, fifth and sixth embodiments 20, 30 and 40, respectively, described above with reference to FIGS. 11–13, 14–16 and 17–19, respectively, are orientated basically perpendicular relative to the bottom wall of the U-shaped fixation members 52 and 54 similar to the bottom wall 24 described above with reference to FIG. 11. Contrary to the exterior side walls of the U-shaped fixation members 52 and 54, the interior side walls of the U-shaped fixation members 52 and 54 slope similar to the interior side wall 23 described above with reference to FIG. 11 which is illustrated by the two sets of dotted lines representing the interior side walls of the lower and upper U-shaped fixation members, which sloping is also evident from FIG. 22. The sloping of the interior side walls of the U-shaped fixation members 52 and 54 basically serves the purpose of ensuring that the interior side walls contact the inner sides of the upper and lower teeth of the user for providing a proper fixation of the entire device relative to the cranium, i.e. the upper and lower parts of the mouth of the user.

Whereas the various embodiments of the device according to the present invention have been described above in relation to the purpose of preventing stertorous breathing or snoring, the device according to the present invention in its above described embodiments and numerous other embodiments which will be evident to a person having ordinary skill in the art and to be contemplated part of the present invention as defined in the appending claims is also adapted to prevent persons or individuals from grinding their teeth during sleep and consequently for preventing the persons or individuals using the device according to the present invention from damaging their teeth. Provided the device according to the present invention is used for preventing individuals or persons grinding their teeth, the tongue catching member such as the U-shaped brace or tongue catching member 65 serving the purpose of keeping the tongue in a forward position may be omitted.

EXAMPLE

A device according to the present invention for preventing stertorous breathing or snoring and also preventing the user from grinding his or her teeth was produced from medical rubber by injection moulding and implemented in accordance with the above described presently preferred fourth embodiment described above with reference to FIGS. 11–13. The device was unitary cast in a single casting or moulding process. Although the individual components or elements of the device vary to some extent providing specific variations of elasticity, flexibility and strength, the below figures represent the average dimensions of the device. The maximum width of the U-shaped fixation member 20 defined by the distance between the opposite ends of the exterior side wall 21 was approximately 63 mm. The average thickness of the exterior side wall 22 was approximately 0.7–0.8 mm and similarly the average thickness of the interior side wall 23 and the average thickness of the bottom wall 24 were approximately 0.7–1.0 mm and approximately 1.5–2.0 mm. The interior distance between the opposite ends of the interior side wall 23, i.e. the maximum span of the girder 26, was approximately 30 mm. The girder 26 defined a substantially plane surface constituting an interior surface illustrated in FIG. 11 and a curved outer surface illustrated in FIG. 12. The minimum width of the girder, i.e. the vertical extension of the girder illustrated in FIG. 13, was approximately 11 mm and the thickness below the U-shaped brace or tongue catching member 27, i.e. the distance from the above described plane surface to the curved surface was approximately 2.0 mm. The U-shaped brace or tongue catching member 27 was of a substantially circular cross-section of a diameter of approximately 5 mm and the maximum height of the U-shaped brace or tongue catching member 27 above the curved surface of the girder 26 illustrated in FIG. 12 was approximately 20 mm. The U-shaped brace or girder sloped approximately 70° from the above plane upper surface defined by the girder 26 and defined a curve as illustrated in FIG. 21. The exterior side wall 22 defined an rearwardly sloping angle of approximately 80° at the foremost arch-shaped area 25, and a height of approximately 14 mm at said area. At the rearmost area opposite to the foremost area 25, i.e. at the upper end of the exterior side wall 22 adjacent to the upper boundary of the girder 26, the height of the exterior side wall was approximately 2.5 mm above the bottom wall 24. The maximum height of the interior side wall 23 adjacent to the foremost arch-shaped area 25 was 7.0–7.5 mm, and the interior side wall 23 defined in angle of approximately 70°–80° sloping rearwardly and substantially parallel with the exterior side wall 22 at the foremost arch-shaped area 25. At the outermost end of the interior side wall 23, the interior side wall 23 was flush with the interior wall defined by the girder 26 illustrated in FIG. 11.

What is claimed is:

1. A device for preventing stertorous breathing or snoring and adapted to be fixated in a person's upper part of the mouth, comprising a non-rigid and flexible transverse girder for fixation in the upper part of a person's mouth, preferably at the back of the upper part of the mouth, and a tongue catching member extending downwardly from said non-rigid and flexible transverse girder said tongue catching member being produced from an elastic material and being adapted to press the tongue in a forward direction and to fixate the tongue in a forward position in order to prevent the tongue from blocking the respiratory passages.

2. The device according to claim 1, said non-rigid and flexible transverse girder being fixated in a person's upper mouth by means of a fixation member adapted to cooperate with the teeth or gums in the user's mouth.

3. The device according to claim 2, said fixation member being adapted to engage with the row of teeth and/or the gums of the upper part of a person's mouth for fixating the device in the user's upper part of mouth.

4. The device according to claim 3, said fixation part being produced from an elastic material for adjustment to the row of teeth and the gums in the upper part of a user's mouth.

5. The device according to claim 4, said fixation part being U-shaped and constituting a groove for engaging with a user's teeth or gums.

6. The device according to claim 5, said groove being perforated or provided with slots for fixation in relation to a user's teeth or gums.

7. The device according to claim 5, said transverse girder being more rigid than the U-shaped part and preferably being of a rigidity so as to ensure that the two legs of the U-shaped part are kept at the same level during use of the device.

8. The device according to claim 5, wherein an exterior wall of the U-shaped member, at least in the area in which it is adapted to engage with the front teeth, extending upwardly and inwardly in relation to a bottom wall in order to press said exterior wall outwardly when said device is positioned and also after said device is positioned for putting a pressure to the teeth for fixation of the device.

9. The device according to claim 6, wherein an interior side wall is lower than an exterior side wall at least in the area adapted to engage with the front teeth.

10. The device according to claim 2, further comprising an additional fixation member adapted to cooperate with the teeth or the gums in the lower part of the user's mouth, said additional fixation member being connected to said fixation member through a hinge and serving the purpose of fixating the lower part of the user's mouth in relation to the upper part of the user's mouth, preferably in a relaxed position.

11. The device according to claim 10, said additional fixation member being made from the same material as the fixation member.

12. The device according to claim 1, said non-rigid and flexible transverse girder and said downwardly protruding tongue catching member being produced from the same non-rigid and elastic material.

13. The device according to claim 1, said tongue catching member having the form of a plate.

14. The device according to claim 1, said tongue catching member being formed as a substantially U-shaped brace.

15. The device according to claim 1, said tongue catching member, seen in profile, being arc-shaped having its cavity facing downwards.

16. The device according to claim 1 said tongue catching member extending crosswise backwardly and downwardly.

17. A device for preventing abrasion of the teeth in the upper and the lower part of the mouth as a result of a person grinding his teeth during sleep, comprising a U-shaped fixation part constituting a groove for catching the user's teeth and gums in the upper part of the user's mouth and being produced from a elastic material for adjustment in relation to the row of teeth and the gums in the upper part of the user's mouth, and further comprising a non-rigid and flexible transverse girder connecting the back ends of the U-shaped fixation part in the back of the upper part of the user's mouth.

18. The device according to claim 17, said groove being perforated or provided with slots for fixation in relation to the teeth and gums of the user.

19. The device according to claim 17, further comprising a tongue catching member protruding downwardly from said non-rigid and flexible transverse girder, said tongue catching member being produced from an elastic material and which being adapted to fixate the tongue in a forward position in order to prevent the tongue from blocking the respiratory passages.

20. Device according to claim 19, said non-rigid and flexible transverse girder and said downwardly protruding tongue catching member being produced from the same flexible and elastic material.

\* \* \* \* \*

UNITED STATES PATENT AND TRADEMARK OFFICE
CERTIFICATE OF CORRECTION

| | | |
|---|---|---|
| PATENT NO. | : 6,467,484 B1 | Page 1 of 1 |
| DATED | : October 22, 2002 | |
| INVENTOR(S) | : Torsten De Voss | |

It is certified that error appears in the above-identified patent and that said Letters Patent is hereby corrected as shown below:

Column 11,
Lines 27-29, please change claim 9 as follows:
-- 9. The device according to claim 5, wherein an interior side wall is lower than an exterior side wall at least in the area adapted to engage with the front teeth. --

Signed and Sealed this

Third Day of February, 2004

JON W. DUDAS
*Acting Director of the United States Patent and Trademark Office*